Figure 1:
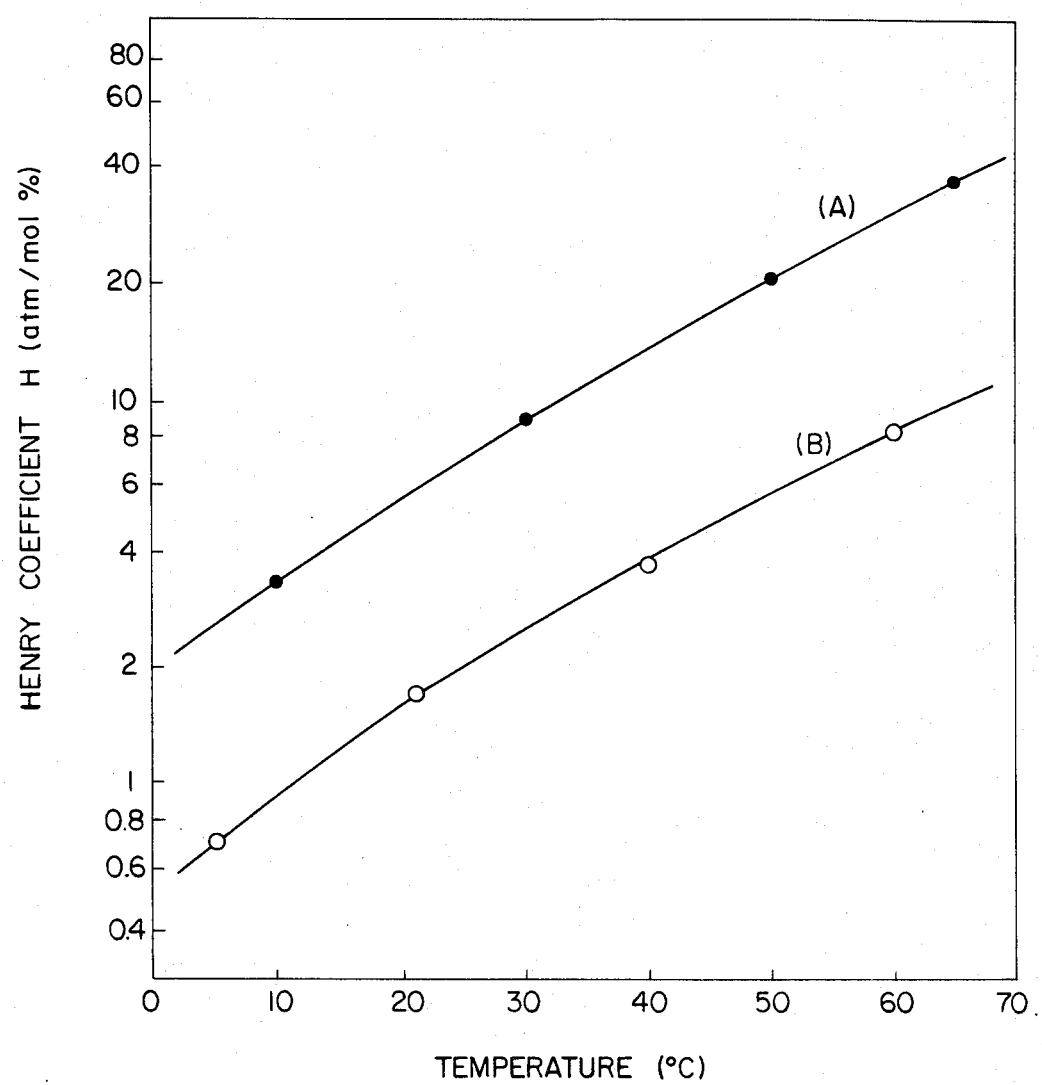

United States Patent [19]

Sada et al.

[11] Patent Number: 4,618,709

[45] Date of Patent: Oct. 21, 1986

[54] WASTE WATER TREATMENT IN THE PRODUCTION OF METHACRYLIC ACID

[75] Inventors: Masao Sada, Nara; Michio Kato, Ehime; Masami Ayano, Ehime; Tadashi Abe, Ehime; Masanori Moriwaki, Ehime, all of Japan

[73] Assignee: Sumitomo Chemical Company, Limited, Osaka, Japan

[21] Appl. No.: 229,844

[22] Filed: Jan. 30, 1981

[30] Foreign Application Priority Data

Feb. 1, 1980 [JP] Japan ................................ 55-11622

[51] Int. Cl.$^4$ ..................... C07C 51/25; C07C 51/48; C07C 57/05; C07C 57/055
[52] U.S. Cl. .................................. 562/532; 562/536; 562/538; 562/545; 562/548; 562/600; 562/608; 568/470; 568/471; 568/476; 568/492
[58] Field of Search ............... 562/608, 532, 534, 535, 562/600, 538, 545; 568/470, 471, 476, 492

[56] References Cited

U.S. PATENT DOCUMENTS 3,781,332  12/1973  Sato et al. ........................... 562/600

FOREIGN PATENT DOCUMENTS

| 108208 | 8/1975 | Japan ................................ 562/513 |
| 30688 | 8/1978 | Japan . | |
| 939713 | 10/1963 | United Kingdom ................ 562/535 |
| 1145778 | 3/1969 | United Kingdom ................ 562/600 |

OTHER PUBLICATIONS

"Make MMA from Spent-BB", by Hasuike et al., Hydrocarbon Processing, Feb. 1979, pp. 105-107.

*Primary Examiner*—Vivian Garner
*Attorney, Agent, or Firm*—Birch, Stewart, Kolasch & Birch

[57] ABSTRACT

A process for separation of methacrylic acid from a methacrylic acid-containing, gaseous reaction mixture obtained by subjecting methacrolein or a compound which can afford methacrolein under reaction conditions and molecular oxygen to gas phase reaction in the presence of a catalyst for oxidation under the coexistence of an inert gas for dilution which comprises (a) cooling the gaseous reaction mixture from a reactor wherein the gas phase reaction has been effected to separate into condensable components including methacrylic acid, acetic acid and water vapor as a condensed liquor and non-condensable components including methacrolein as a non-condensed gaseous mixture, (b) eliminating contaminating methacrolein from the condensed liquor and (c) contacting the resulting condensed liquor with an organic solvent to extract methacrylic acid, followed by separation into an organic solvent solution including methacrylic acid and an aqueous solution as waste water, characterized in that (1) the inert gas for dilution is a non-condensable gas or its mixture with water vapor and (2) the aqueous solution ultimately separated is evaporated and the evolved vapor is subjected to catalytic combustion with molecular oxygen, whereby the amount of waste water to be discharged is much suppressed.

9 Claims, 2 Drawing Figures

WASTE WATER TREATMENT IN THE PRODUCTION OF METHACRYLIC ACID

The present invention relates to waste water treatment in the production of methacrylic acid. More particularly, it relates to an improved process for production of methacrylic acid by gas phase catalytic oxidation of methacrolein or its precursor with molecular oxygen in the presence of an oxidation catalyst wherein the discharge of waste water is markedly suppressed so as not to cause any pollution problem.

The expression "methacrolein or its precursor" is intended to mean methacrolein or any compound which can afford methacrolein under reaction conditions such as isobutylene or t-butyl alcohol.

As well known, methacrylic acid can be manufactured by gas phase catalytic oxidation of methacrolein or its precursor with molecular oxygen in the presence of an oxidation catalyst. Usually, the oxidation is carried out in the coexistence of an inert gas for dilution. As the result, the gaseous reaction mixture from 8 oxidation contains, in addition to methacrylic acid as the objective product, methacrolein, acetic acid, carbon monoxide, carbon dioxide, water, oxygen, nitrogen, etc. Such gaseous reaction mixture is subjected to cooling, whereby condensable gaseous components (e.g. methacrylic acid, acetic acid) are condensed as a condensed liquor and separated from non-condensable gaseous components (e.g. methacrolein) as a non-condensed gaseous mixture. The non-condensed gaseous mixture is, are, after recovery of unreacted methacrolein therefrom, subjected to catalytic combustion in the presence of molecular oxygen to burn any combustible component therein, and the resulting pollution-free gas is released into atmosphere. On the other hand, the condensed liquor is, after recovery of unreacted methacrolein therefrom, treated with an appropriate organic solvent such as xylenemethyl methacrylate to extract methacrylic acid. The resultant aqueous solution is subjected to distillation for recovery of the extraction solvent dissolved therein and then discharged as waste water.

As stated above, said oxidation is usually performed in the coexistence of any inert gas for dilution. This is on one hand effective in preventing explosion and on the other hand effective in controlling the generation of heat. Examples of the inert gas are nitrogen, water vapor, exhaust gas, etc. Among them, water vapor is the most frequently employed. However, since it is necessary to use water vapor in an amount as great as 10 to 50 mol per one mol of methacrolein or its precursor, there is necessarily produced a large amount of condensed water in a condenser so that the produced aqueous solution containing methacrylic acid is voluminous and the concentration of methacrylic acid in such aqueous solution is small. Thus, a large quantity of an organic solvent is needed for extraction of methacrylic acid from said aqueous solution, and also the amount of waste water to be discharged becomes great. These make the purification of methacrylic acid and the treatment of waste water extremely disadvantageous from an economical viewpoint.

While many oxidation catalysts have been developed for the production of methacrylic acid from methacrolein or its precursor by gas phase catalytic oxidation with molecular oxygen, their performances are not yet satisfactory to obtain methacrylic acid in industrially good yields. Thus, there are usually by-produced large quantities of carbon monoxide, carbon dioxide, acetic acid, etc. The quantity of acetic acid is particularly large and amounts to, for example, 30 to 60 mol per 100 mol of methacrylic acid. On the extraction of methacrylic acid with an organic solvent, only a part of the acetic acid enters the organic solvent phase due to the difference in distribution coefficient, and the greater part remains in the aqueous phase and is ultimately discharged as waste water.

The waste water contains acetic acid as the main component, and the total concentration of organic substances therein usually amounts to 1–5% by weight. Since the chemical oxygen demand (COD) is too high to apply ordinary biochemical treatment such as activated sludge process thereto, pre-treatment such as wet oxidation treatment or combustion in liquid is required. Further, the quantity of the waste water is quite large so that a very high cost is needed for its treatment. Recovery of acetic acid from the waste water by distillation or combination of extraction and distillation may be thought of, but too large quantities of energy are required to treat such an enormous quantity of the waste water having an acid concentration as low as less than 5% by weight. Consequently, it is highly demanded to establish efficient treatment of the waste water or to modify the quality and quantity of the waste water so as to be easily treated.

Japanese Patent Publication (unexamined) No. 44609/1979 discloses a process wherein water, by-produced in the manufacture of acrylic acid by gas phase catalytic oxidation of propylene, is recycled for use as an absorption liquor for collection of the oxidation products. In this process, propylene is converted into acrylic acid by gas phase catalytic oxidation, the produced acrylic acid is condensed by cooling and collected, and a part of the non-condensed gas is recycled as the feed gas. Waste water, obtained after separation of acrylic acid from the condensed aqueous acrylic acid solution, is treated with an alkaline substance, purified by the reverse osmosis membrane technique and recycled for use as an absorption liquor for collection of acrylic acid from the gaseous reaction mixture in the oxidation. This process is quite efficient for treatment of waste water in the acrylic acid production. However, its application to waste water treatment in the methacrylic acid production encounters great difficulties, because of the difference of the components in the reaction mixture.

In the methacrylic acid production, oxidation catalysts of high performances enough to be comparable to those for the acrylic acid production, are not yet developed, and because of their poor selectivity, they produce many organic compounds as by-products, particularly acetic acid in large amounts. As stated above, acetic acid amounts to as much as 30 to 60 mol per 100 mol of methacrylic acid. In order to neutralize such acetic acid containing water, a large amount of an alkaline substance is needed. Further, a large amount of acetic acid is simply wasted by said neutralization. Furthermore, application of the reverse osmosis membrane technique is limited to the case wherein the quantity of waste water is relatively small. Because of these reasons, the industrial application of said conventional process to treatment of waste water in the methacrylic acid production is not suitable.

Japanese Patent Publication (unexamined) No. 52027/1979 also discloses a process wherein the gaseous reaction mixture obtained from the gas phase catalytic oxidation of methacrolein or its precursor with molecular oxygen is cooled in a condenser to separate into an aqueous methacrylic acid solution and an unreacted methacrolein-containing gas, the gas is contacted with the aqueous liquor obtained from the aqueous methacrylic acid solution by stripping methacrolein therefrom so as to absorb methacrolein therein and the methacrolein-absorbed solution as well as the aqueous methacrylic acid solution are subjected to stripping of methacrolein and the stripped methacrolein-containing gas is recycled to the inlet of a reactor for the oxidation. In this process, the most characteristic feature resides in that the aqueous methacrylic acid solution produced therein is used as an absorption liquor for methacrolein and such use produces an effective and efficient result. However, the problem of waste water treatment still remains.

It has now been found that the use of a non-condensable gas or its mixture with water vapor as the inert gas for dilution of the feed gas in the gas phase catalytic oxidation of methacrolein or its precursor with molecular oxygen for production of methacrylic acid is quite effective in decreasing the amount of the condensed liquor obtainable by cooling the gaseous reaction mixture in said oxidation and maintaining a high concentration of methacrylic acid in such condensed liquor. As a result, recovery of methacrylic acid from the condensed liquor can be accomplished with ease. In addition, the evaporation of the waste water obtained from the condensed liquor by separation of methacrylic acid and methacrolein therefrom and the catalytic combustion of the resulting vapor with molecular oxygen make it possible to achieve the treatment of the waste water at a remarkably low cost.

According to the present invention, there is provided a process for separation of methacrylic acid from a methacrylic acid-containing, gaseous reaction mixture obtained by subjecting methacrolein or its precursor and molecular oxygen to gas phase reaction in the presence of a catalyst for oxidation under the coexistence of an inert gas for dilution which comprises (a) cooling the gaseous reaction mixture from a reactor wherein the gas phase reaction has been effected to separate into condensable components including methacrylic acid, acetic acid and water vapor as a condensed liquor and non-condensable components including methacrolein as a non-condensed gaseous mixture, (b) eliminating contaminating methacrolein from the condensed liquor and (c) contacting the resulting condensed liquor with an organic solvent to extract methacrylic acid, followed by separation into an organic solvent solution including methacrylic acid and an aqueous solution as waste water, characterized in that (1) the inert gas for dilution is a non-condensable gas or its mixture with water vapor and (2) the aqueous solution ultimately separated is evaporated and the evolved vapor is subjected to catalytic combustion with molecular oxygen. By such process, the amount of waste water to be discharged is markedly decreased.

The expression "non-condensable gas" is intended to mean any gas which is substantially inert to any component in the feed gas and the produced gas under reaction conditions as adopted and which is materially not condensed under cooling conditions as applied. Examples of the non-condensable gas are nitrogen, carbon dioxide, etc. Exhaust gas obtained from the gaseous reaction mixture by separation of methacrylic acid and methacrolein therefrom is also usable. The exhaust gas may be recycled as such, but preferably it is recycled after organic components in it have been brought into catalytic combustion together with molecular oxygen. When non-condensable gas is used in a mixture with water vapor, the concentration of water vapor in the feed gas may be less than 20 mol %, preferably less than 10 mol %, more preferably less than 5 mol %. The concentration of more than 20 mol % lowers the concentration of methacrylic acid in the condensed liquor obtained by cooling of the gaseous reaction mixture, which makes disadvantageous separation and recovery of methacrylic acid. Further, it increases the amount of waste water so that a large cost is needed for treatment of waste water.

For cooling rapidly the gaseous reaction mixture, the condenser is operated usually at a temperature lower than 100° C., preferably of from 30° to 80° C. Operating temperatures higher than 100° C. are not desirable because methacrylic acid polymerizes to cause its loss and troubles.

The condenser may be circulated with the condensed liquor produced therein by cooling the gaseous reaction mixture. When the methacrylic acid concentration in the condensed liquor is so high as being polymerized with ease, a portion of the waste water containing acetic acid in a high concentration obtained from the condensed liquor by separation of methacrylic acid therefrom may be used for circulation. The cooling operation may be controlled so as to adjust the methacrylic acid concentration in the condensed liquor to be not more than 50% by weight, preferably not more than 40% by weight.

Since the condensed liquor and the non-condensed gaseous mixture separated from each other in the condenser contain unreacted methacrolein, the methacrolein may be recovered therefrom by any conventional procedure such as distillation, extraction, absorption or stripping. One of typical procedures for recovery comprises treatment with an aqueous methacrylic acid solution as an absorption liquor at a temperature of not higher than 30° C., preferably of from 0° to 15° C., as disclosed in Japanese Patent Publication (unexamined) No. 52027/1979.

In usual absorption processes, it is common to decrease the quantity of a non-condensable gas, because its increase results in lowering the absorption efficiency. In the present invention, a non-condensable gas is rather positively and intentionally used, and this may be considered as disadvantageous from the viewpoint of methacrolein-absorbing efficiency. Actually, however, the aqueous methacrylic acid solution as an absorption liquor has a sufficient absorption efficiency. The methacrolein-absorbing efficiency of the aqueous methacrylic acid solution becomes high as an increase in the methacrylic acid concentration, and it can further be elevated by the addition of acetic acid to this system. These are evidenced by FIG. 1 of the accompanying drawing, which shows Henry coefficients of methacrolein in an aqueous methacrylic acid solution (referred to as an absorption liquor (A)) and in an aqueous methacrylic acid solution containing acetic acid (referred to as an absorption liquor (B)), the absorption liquor (A) comprising methacrylic acid and water in a weight ratio of 12:88 and the absorption liquor (B) comprising methacrylic acid, acetic acid and water in a weight ratio of 30:20:50.

From the aqueous methacrylic acid solution, from which methacrolein has been removed, methacrylic acid is separated by extraction. For instance, the aqueous methacrylic acid solution is extracted with an organic solvent such as methyl methacrylate/xylene to give an organic solvent solution including methacrylic acid and the residual water, of which the former is used for the production of methacrylic acid or methyl methacrylate and the latter is separated by distillation into the extraction solvent and the waste water containing acetic acid in a high concentration.

Said waste water is evaporated, and the vapor evolved is brought into contact with molecular oxygen in the presence of an oxidation catalyst for catalytic combustion of volatile organic compounds such as acetic acid included therein and then discharged into atmosphere. The residue after evaporation is self-combustible, high boiling organic compounds and may be burned in a conventional combustion equipment such as a combustion furnace, an apparatus for combustion in liquid or a wet oxidation apparatus.

The quantity of evaporation may be determined taking into account the following points: (1) the residue after evaporation is self-combustible; (2) scaling on the evaporator wall should be prevented; and (3) elevating the boiling point in the evaporator in vain requires high-temperature heat sources. In the process of this invention, the amount of evaporation may be usually not less than 70% by weight, preferably not less than 85% by weight, of the waste water supplied.

On the catalytic combustion of the vapor evolved, heat of combustion is produced in considerable quantities and may be recovered and re-used. Further, a part of said waste water may be recycled, before evaporation, to the condenser, if necessary.

Figure 2:
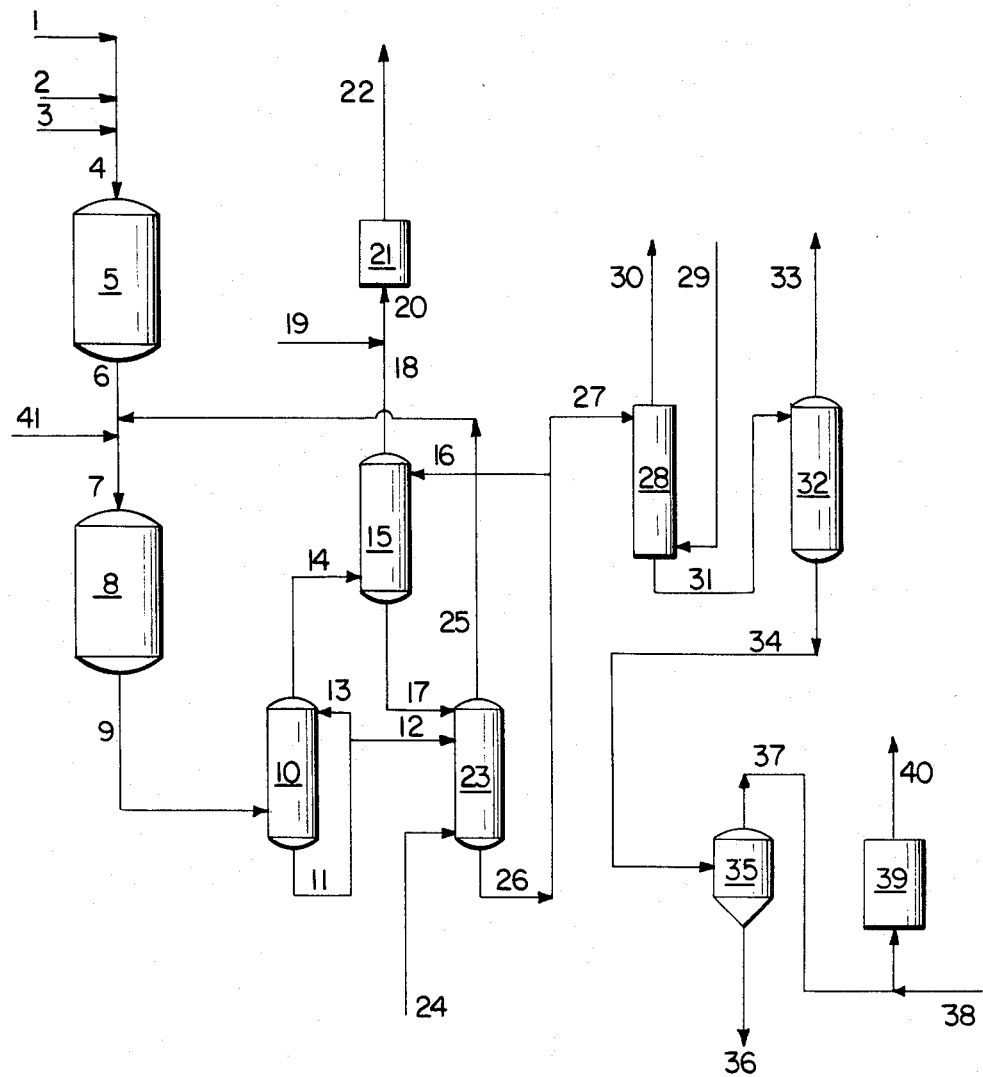

The process of this invention will be illustrated more in detail with reference to FIG. 2 of the accompanying drawing, which is a flow sheet showing the production of methacrylic acid by the use of two oxidation reactors connected in series and the recovery of methacrolein by stripping and absorption. However, it should not be understood that this invention is limited to this embodiment.

In FIG. 2, isobutylene and/or t-butyl alcohol are supplied to a first-stage oxidation reactor 5 through lines 1 and 4 and converted to methacrolein by gas phase catalytic oxidation with air supplied through lines 2 and 4. Through lines 3 and 4 is supplied an inert gas for dilution of the feed gas such as nitrogen, carbon dioxide gas and/or exhaust gas discharged from a combustion equipment 21 through a line 22. When desired, water vapor also may be supplied through lines 3 and 4, but it is advantageous to minimize the quantity of water vapor from the viewpoint of waste water treatment. The outlet gas of the reactor 5 is withdrawn through a line 6 and sent to a second-stage oxidation reactor 8 through a line 7. At the same time, a methacrolein-containing gas from a methacrolein-stripping tower 23 is sent to the reactor 8 through lines 25 and 7. In the reactor 8, methacrolein is converted to methacrylic acid by gas phase catalytic oxidation, if necessary, with air supplied through lines 41 and 7. The gaseous reaction mixture from the reactor 8 is supplied to the bottom of a rapid-cooling condenser 10 through a line 9 and brought into direct countercurrent contact with a methacrylic acid-containing condensed liquor circulated through lines 11 and 13, whereby methacrylic acid, methacrolein, acetic acid, water vapor and the like in the gaseous reaction mixtuture are condensed.

The overhead gas of the condenser 10 is supplied to the bottom of a methacrolein-absorbing tower 15 through a line 14. The condensed liquor from the condenser 10 is supplied to the top of the tower 23 through lines 11 and 12, and methacrolein contained therein is stripped by an inert gas such as nitrogen or carbon dioxide gas supplied through a line 24, or by exhaust gas from the line 22 supplied through line 24. A gas containing stripped methacrolein is circulated to the reactor 8, while an aqueous solution containing methacrylic acid and acetic acid as a by-product is withdrawn from the bottom of the tower 23 through a line 26.

The aqueous solution containing methacrylic acid and acetic acid as main components, from which methacrolein has been removed almost completely, is supplied to the top of a methacrylic acid-extracting tower 28 through lines 26 and 27. Also, a part of this aqueous solution is supplied to the top of the tower 15 through a line 16 as an absorbing solvent for methacrolein contained in the overhead exhaust gas of the condenser 10 coming through the line 14.

Most of methacrolein contained in said overhead gas is absorbed by the absorbing solvent during the gas/liquid countercurrent contact in the tower 15, and the exhaust gas from the tower 15 is sent to the combustion equipment 21 through lines 18 and 20. A liquor containing absorbed methacrolein is withdrawn from the bottom of the tower 15 through a line 17 and supplied to the top of the tower 23. Methacrolein in the liquors supplied to the tower respectively through lines 17 and 12 is stripped by an inert gas supplied through the line 24 and circulated to the inlet of the reactor 8 from the top of the tower 23 through the lines 25 and 7.

Combustible gases such as carbon monoxide, contained in the above exhaust gas supplied to the combustion equipment 21 through the lines 18 and 20, are almost completely burned there, if necessary, with air supplied through a line 19, and the pollution-free exhaust gas thus formed is released into atmosphere through the line 22. A part of the pollution-free exhaust gas may be recycled through the line 3 to dilute isobutylene and/or t-butyl alcohol supplied through the line 1 as well as air supplied through the line 2.

From the aqueous solution containing methacrylic acid and acetic acid as main components supplied to the top of the methacrylic acid-extracting tower 28 through the line 27, methacrylic acid is removed by extraction with an extracting solvent supplied to the bottom of the tower 28 through a line 29. The solvent after extracting methacrylic acid is withdrawn from the top of the tower 28 and supplied to the methacrylic acid-purifying step through a line 30.

The residual water containing acetic acid in high concentrations is withdrawn from the bottom of the tower 28 and supplied to the upper part of an extracting solvent recovering tower 32 through a line 31, and the solvent accompanying the residual water is recovered from the top of the tower through a line 33. From the bottom of the tower 32 is withdrawn a bottom liquor containing acetic acid in high concentrations.

Most of the waste water withdrawn through a line 34 is evaporated in an evaporator 35, and vapor evolved is led to a catalytic combustion equipment 39 through a line 37, burned with air supplied through a line 38 to make pollution-free and released into atmosphere through a line 40. The residue after evaporation is withdrawn from the evaporator 35 through a line 36, burned in a combustion furnace and then discharged.

The present invention will be illustrated with reference to the following examples, which are not however to be interpreted as limiting the invention thereto.

EXAMPLE 1

According to the flow sheet shown in FIG. 2, the gas phase catalytic oxidation for production of methacrylic acid was carried out by supplying a 85 weight % aqueous solution of t-butyl alcohol through the line 1 and exhaust gas from the line 22 through the lines 3 and 24 but supplying no air through the line 19. Each equipment was operated under the conditions as shown in Table 1. As the result, the gas lines and liquid lines in the flow sheet gave, at each part thereof, the compositions and flow amounts as shown in Tables 2 and 3, respectively.

TABLE 1

| | Unit | Rapid-cooling condenser 10 | Methacrolein-absorbing tower 15 | Methacrolein-stripping tower 23 | Methacrylic acid-extracting tower 28 | Extracting solvent-separating tower 32 | Evaporator 35 | Catalytic combustion equipment 39 |
|---|---|---|---|---|---|---|---|---|
| Form | | Packed tower | Packed tower | Packed tower | Pulsed extraction column | Packed tower | External heating type | Fixed-bed type |
| Material of tower | | Stainless steel | Stainless steel | Stainless steel | Stainless steel | Stainless steel | Stainless steel | Stainless steel |
| Packing | | 15 $\phi$ Raschig ring | 10 $\phi$ Raschig ring | 10 $\phi$ Raschig ring | Perforated plate | 10 $\phi$ Raschig ring | — | Pt catalyst supported |
| Material of packing | | Porcelain | Porcelain | Porcelain | Stainless steel | Stainless steel | — | — |
| Diameter of tower | mm | 100 | 50 | 50 | 50 | 50 | 200 | 50 |
| Condensation part | mm | 2000 | 6000 | 3000 | 40 plates | — | 500 (height) | 200 (height of catalyst layer) |
| Recovery part | mm | 2000 | 6000 | 3000 | 40 plates | 3000 | 500 (height) | 200 (height of catalyst layer) |
| Operating pressure | atm | 1.5 | 1.5 | 2.5 | 1 | 1 | 1.5 | 1.5 |
| Bottom temperature | °C. | 50 | 10 | 60 | 30 | 100 | 115 | 250 (at inlet of catalyst layer) |
| Reflux ratio | | — | — | — | — | 4.0 | — | — |

TABLE 2

| | Unit | 1 | 2 | 3 | 7 | 9 | 14 | 18 | 22 | 24 | 25 | 38 | 40 | 41 |
|---|---|---|---|---|---|---|---|---|---|---|---|---|---|---|
| Oxygen | mol/% | — | 21.00 | 4.80 | 7.29 | 4.89 | 5.51 | 5.73 | 4.80 | 4.80 | 4.01 | 21.00 | 12.47 | 21.00 |
| Nitrogen | " | — | 79.00 | 87.49 | 74.14 | 74.32 | 83.78 | 87.04 | 87.49 | 87.49 | 73.01 | 79.00 | 58.63 | 79.00 |
| Carbon monoxide | " | — | — | — | 0.33 | 1.04 | 1.17 | 1.21 | — | — | — | — | — | — |
| Carbon dioxide | " | — | — | 6.99 | 3.99 | 4.62 | 5.21 | 5.41 | 6.99 | 6.99 | 5.83 | — | 3.11 | — |
| t-Butyl alcohol | " | 57.95 | — | — | 0.05 | — | — | — | — | — | — | — | — | — |
| Meth- | " | — | — | — | 3.02 | 1.21 | 1.28 | 0.06 | — | — | 5.31 | — | — | — |

TABLE 2-continued

|  | Unit | Line No. | | | | | | | | | | | |
|---|---|---|---|---|---|---|---|---|---|---|---|---|---|
|  |  | 1 | 2 | 3 | 7 | 9 | 14 | 18 | 22 | 24 | 25 | 38 | 40 | 41 |
| acrolein |  |  |  |  |  |  |  |  |  |  |  |  |  |  |
| Methacrylic acid | " | — | — | — | 0.08 | 1.53 | — | — | — | — | — | — | — | — |
| Acetic acid | " | — | — | — | 0.20 | 0.63 | 0.03 | — | — | — | 0.08 | — | — | — |
| Acetone*1 | " | — | — | — | 0.31 | 0.06 | 0.04 | — | — | — | 0.18 | — | — | — |
| Acrylic*2 acid | " | — | — | — | — | 0.02 | — | — | — | — | — | — | — | — |
| Water | " | 42.05 | — | 0.72 | 10.59 | 11.68 | 2.99 | 0.55 | 0.72 | 0.72 | 11.58 | — | 25.79 | — |
| Flow amount | mol/hr | 9.3 | 61 | 63 | 213 | 213 | 189 | 182 | 181 | 39 | 46 | 58.43 | 78.73 | 28 |

Note:
*1 By-products having a lower boiling point than that of acetic acid are represented by acetone (same applies hereinafter).
*2 By-products having a higher boiling point than that of acetic acid are represented by acrylic acid (same applies hereinafter).

TABLE 3

|  | Unit | Line No. | | | | | | | |
|---|---|---|---|---|---|---|---|---|---|
|  |  | 12 | 16 | 26 | 29 | 30 | 33 | 34 | 36 |
| Methacrolein | wt % | 1.51 | 0.04 | 0.04 | 0.60 | 0.39 | 1.93 | — | — |
| Methacrylic acid | " | 39.37 | 40.45 | 40.45 | 0.14 | 40.26 | — | 0.10 | 0.11 |
| Acetic acid | " | 10.53 | 10.99 | 10.99 | 5.74 | 3.68 | — | 18.44 | 27.42 |
| Acetone | " | 0.52 | 0.42 | 0.42 | 0.84 | 0.46 | 56.59 | — | — |
| Acrylic acid | " | 0.47 | 0.42 | 0.42 | 0.41 | 0.38 | — | 0.49 | 2.58 |
| Water | " | 47.60 | 47.67 | 47.67 | 1.68 | 1.05 | 2.81 | 80.97 | 69.89 |
| Methyl methacrylate | " | — | — | — | 25.38 | 15.03 | 26.19 | — | — |
| Xylene | " | — | — | — | 65.21 | 39.08 | 12.48 | — | — |
| Flow amount | g/hr | 710 | 2075 | 2767 | 418 | 695 | 6 | 404 | 7.1 |

EXAMPLE 2

Operation was carried out in the same manner as in Example 1 except that isobutylene was supplied through the line 1, nitrogen gas was supplied through the lines 3 and 24 and the aqueous solution obtained through the line 34 was circulated with a rate of 100 g/hr to the rapid-cooling condenser 10. As the result, the gas lines and liquid lines gave, at each part thereof, the compositions and flow amounts as shown in Tables 4 and 5, respectively.

TABLE 4

|  | Unit | Line No. | | | | | | | | | | | |
|---|---|---|---|---|---|---|---|---|---|---|---|---|---|
|  |  | 1 | 2 | 3 | 7 | 9 | 14 | 18 | 22 | 24 | 25 | 38 | 40 | 41 |
| Oxygen | mol/% | — | 21.00 | — | 6.89 | 4.62 | 4.92 | 5.10 | 4.31 | — | — | 21.00 | 13.16 | 21.00 |
| Nitrogen | " | — | 79.00 | 100 | 83.02 | 82.99 | 88.56 | 91.89 | 92.34 | 100 | 82.94 | 79.00 | 61.89 | 79.00 |
| Carbon monoxide | " | — | — | — | 0.32 | 0.98 | 1.05 | 1.09 | — | — | — | — | 3.29 | — |
| Carbon dioxide | " | — | — | — | 0.63 | 1.21 | 1.28 | 1.33 | 2.64 | — | — | — | — | — |
| Isobutylene | " | 100 | — | — | 0.05 | — | — | — | — | — | — | — | — | — |
| Methacrolein | " | — | — | — | 2.88 | 1.14 | 1.14 | 0.05 | — | — | 5.29 | — | — | — |
| Methacrylic acid | " | — | — | — | 0.08 | 1.45 | — | — | — | — | — | — | — | — |
| Acetic acid | " | — | — | — | 0.17 | 0.60 | 0.03 | — | — | — | 0.08 | — | — | — |
| Acetone | " | — | — | — | 0.26 | 0.06 | 0.04 | — | — | — | 0.18 | — | — | — |
| Acrylic acid | " | — | — | — | — | 0.02 | — | — | — | — | — | — | — | — |
| Water | " | — | — | — | 5.70 | 6.72 | 2.98 | 0.54 | 0.70 | — | 11.51 | — | 21.66 | — |
| Flow amount | mole/hr | 5.4 | 75 | 60 | 223 | 225 | 212 | 204 | 203 | 39 | 47 | 53.38 | 68.14 | 37 |

TABLE 5

|  | Unit | Line No. | | | | | | | |
|---|---|---|---|---|---|---|---|---|---|
|  |  | 12 | 16 | 26 | 29 | 30 | 33 | 34 | 36 |
| Methacrolein | wt % | 1.64 | 0.02 | 0.02 | 0.19 | 0.13 | 0.75 | — | — |
| Methacrylic acid | " | 44.37 | 45.24 | 45.24 | 0.09 | 34.25 | — | 0.10 | 0.11 |
| Acetic acid | " | 17.29 | 17.88 | 17.88 | 4.63 | 2.83 | — | 22.24 | 27.08 |
| Acetone | " | 0.46 | 0.47 | 0.47 | 0.65 | 0.37 | 50.90 | — | — |
| Acrylic acid | " | 0.70 | 0.71 | 0.71 | 0.06 | 0.04 | — | 1.17 | 1.53 |
| Water | " | 35.55 | 35.68 | 35.68 | 1.78 | 1.19 | 2.24 | 76.49 | 71.27 |
| Methyl methacrylate | " | — | — | — | 27.78 | 18.18 | 35.67 | — | — |

TABLE 5-continued

|  | Unit | Line No. | | | | | | | |
| --- | --- | --- | --- | --- | --- | --- | --- | --- | --- |
|  |  | 12 | 16 | 26 | 29 | 30 | 33 | 34 | 36 |
| Xylene | " | — | — | — | 64.82 | 43.01 | 10.45 | — | — |
| Flow amount | g/hr | 633 | 1863 | 2484 | 540 | 812 | 7 | 340 | 47.4 |

EXAMPLE 3

Operation was carried out in the same manner as in Example 1 except that t-butyl alcohol was supplied through the line 1, carbon dioxide gas and water vapor were supplied through the line 3 and carbon dioxide gas was supplied through the line 24. As the result, the gas lines and liquid lines gave, at each part thereof, the compositions and flow amounts as shown in Tables 6 and 7, respectively.

TABLE 6

|  | Unit | Line No. | | | | | | | | | | | | |
| --- | --- | --- | --- | --- | --- | --- | --- | --- | --- | --- | --- | --- | --- |
|  |  | 1 | 2 | 3 | 7 | 9 | 14 | 18 | 22 | 24 | 25 | 38 | 40 | 41 |
| Oxygen | mol/% | — | 21.00 | — | 6.76 | 4.54 | 5.22 | 5.42 | 4.58 | — | — | 21.00 | 12.38 | 21.00 |
| Nitrogen | " | — | 79.00 | — | 38.56 | 38.63 | 44.43 | 46.14 | 46.38 | — | — | 79.00 | 58.22 | 79.00 |
| Carbon monoxide | " | — | — | — | 0.30 | 0.97 | 1.11 | 1.15 | — | — | — | — | — | — |
| Carbon dioxide | " | — | — | 80.00 | 38.45 | 39.12 | 44.98 | 46.71 | 48.34 | 100 | 82.85 | — | 3.07 | — |
| t-Butyl alcohol | " | 100 | — | — | 0.05 | — | — | — | — | — | — | — | — | — |
| Methacrolein | " | — | — | — | 2.81 | 1.13 | 1.21 | 0.06 | — | — | 5.31 | — | — | — |
| Methacrylic acid | " | — | — | — | 0.08 | 1.42 | — | — | — | — | — | — | — | — |
| Acetic acid | " | — | — | — | 0.19 | 0.59 | 0.03 | — | — | — | 0.08 | — | — | — |
| Acetone | " | — | — | — | 0.28 | 0.06 | 0.04 | — | — | — | 0.18 | — | — | — |
| Acrylic acid | " | — | — | — | — | 0.02 | — | — | — | — | — | — | — | — |
| Water | " | — | — | 20.00 | 10.82 | 11.84 | 2.99 | 0.53 | 0.70 | — | 11.58 | — | 26.33 | — |
| Flow amount | mol/hr | 5.4 | 75 | 60 | 230 | 229 | 199 | 192 | 191 | 39 | 46 | 64.07 | 86.94 | 37 |

TABLE 7

|  | Unit | Line No. | | | | | | | |
| --- | --- | --- | --- | --- | --- | --- | --- | --- | --- |
|  |  | 12 | 16 | 26 | 29 | 30 | 33 | 34 | 36 |
| Methacrolein | wt % | 1.48 | 0.02 | 0.02 | 0.02 | 0.03 | 1.13 | — | — |
| Methacrylic acid | " | 37.08 | 37.94 | 37.94 | 0.10 | 33.74 | — | 0.74 | 2.47 |
| Acetic acid | " | 10.20 | 10.64 | 10.64 | 5.53 | 4.04 | — | 16.60 | 25.15 |
| Acetone | " | 0.40 | 0.37 | 0.37 | 0.24 | 0.26 | 42.86 | — | — |
| Acrylic acid | " | 0.41 | 0.42 | 0.42 | 0.20 | 0.20 | — | 0.58 | 1.36 |
| Water | " | 50.44 | 50.60 | 50.60 | 1.65 | 1.21 | 3.40 | 82.08 | 71.01 |
| Methyl methacrylate | " | — | — | — | 27.67 | 18.05 | 35.60 | — | — |
| Xylene | " | — | — | — | 64.57 | 42.47 | 17.01 | — | — |
| Flow amount | g/hr | 756 | 2216 | 2955 | 542 | 822 | 4.4 | 454 | 10.4 |

What is claimed is:

1. A process for separation of methacrylic acid from a methacrylic acid-containing gaseous reaction mixture, comprising the steps of:
   (a) cooling a gaseous reaction mixture, which has been obtained by subjecting methacrolein or a compound which can produce methacrolein under reaction conditions and molecular oxygen to a gas phase oxidation reaction in the presence of an oxidation catalyst in the presence of an inert non-condensable dilution gas or a mixture thereof with water vapor in a concentration of less than 20 mol %, to separate said gaseous reaction mixture into condensable components including methacrylic acid, acetic acid and water as a condensed liquor and non-condensable components including methacrolein as a non-condensed gaseous mixture;
   (b) separating contaminating methacrolein from the condensed liquor to form a condensed liquor and an exhaust gas;
   (c) recycling exhaust gas from step (b) for use as said inert non-condensable dilution gas;
   (d) contacting the condensed liquor with an organic solvent to extract methacrylic acid, followed by separation into an organic solvent solution including methacrylic acid and a waste water solution;
   (e) evaporating the waste water solution; and
   (f) subjecting the waste water vapor to catalytic combustion with molecular oxygen.

2. The process according to claim 1, wherein said non-condensable gas which is recycled is subjected to catalytic combustion with molecular oxygen before being recycled.

3. The process according to claim 1, wherein during evaporation the weight of the waste water solution is reduced to below 30% be weight on the basis of the weight before evaporation.

4. A process for separation of methacrylic acid from a methacrylic acid-containing, gaseous reaction mixture, comprising the steps of:

(a) cooling a gaseous reaction mixture, which has been obtained by subjecting methacrolein or a compound which can produce methacrolein under reaction conditions and molecular oxygen to a gas phase oxidation reaction in the presence of an oxidation catalyst in the presence of an inert non-condensable dilution gas or a mixture thereof with water vapor, to separate said gaseous reaction mixture into condensable components including methacrylic acid, acetic acid and water as a condensed liquor and non-condensable components including methacrolein as a non-condensed gaseous mixture;

(b) separating said gaseous mixture in step (a) to form a methacrolein liquor and an exhaust gas;

(c) recycling said exhaust gas from step (b) for use as said inert non-condensable dilution gas while maintaining the concentration of water vapor in the feed gas to said oxidation reaction to less than 20 mol %;

(d) contacting the condensed liquor with an organic solvent to extract methacrylic acid, followed by separation into an organic solvent solution including methacrylic acid and a waste water solution;

(e) evaporating the waste water solution; and (f) subjecting the waste water vapor to catalytic combustion with molecular oxygen.

5. A process for the preparation and purification of methacrylic acid, comprising the steps of:

(a) subjecting methacrolein or a compound which can produce methacrolein under reaction conditions and molecular oxygen to a gas phase oxidation reaction in the presence of an oxidation catalyst in the presence of an inert non-condensable dilution gas or a mixture thereof with water vapor to form a gaseous reaction mixture;

(b) cooling said gaseous reaction mixture to separate said gaseous reaction mixture into condensable components including methacrylic acid, acetic acid and water as a condensable liquor and non-condensable components including methacrolein as a non-condensed gaseous mixture;

(c) separating said methacrolein-containing gaseous mixture from step (b) into a methacrolein liquor and exhaust gas;

(d) recycling said exhaust gas from step (c) to said oxidation step while maintaining the concentration of water vapor in the feed gas to said oxidation reaction to less than 20 mol %;

(e) stripping methacrolein from said methacrolein liquor to form an aqueous solution containing methacrylic acid and acetic acid and to form a methacrolein-containing gas;

(f) contacting said aqueous solution with an organic solvent to extract methacrylic acid, followed by separation into an organic solvent solution including methacrylic acid and a waste water solution;

(g) evaporating the waste water solution; and (h) subjecting the waste water vapor to catalytic combustion with molecular oxygen to obtain pollution-free exhaust.

6. The process according to claim 5, wherein said oxidation is carried out in a first stage oxidation and a second stage and wherein said exhaust gas from step (c) is recycled to said first stage of oxidation.

7. The process according to claim 6, wherein said methacrolein-containing gas from step (e) is introduced into said second stage of oxidation.

8. The process according to claim 5, wherein the concentration of water in said feed gas is maintained to less than 10 mol %.

9. The process according to claim 5, wherein the concentration of water in said feed gas is maintained to less than 5 mol %.

* * * * *